(12) United States Patent
O'Shea et al.

(10) Patent No.: US 7,154,005 B2
(45) Date of Patent: Dec. 26, 2006

(54) SYNTHESIS OF ALPHA FLUOROALKYL AMINES

(75) Inventors: Paul O'Shea, Westmont (CA); Francis Gosselin, Montreal (CA)

(73) Assignee: Merck Frosst Canada, Ltd., Kirkland (CA)

( * ) Notice: Subject to any disclaimer, the term of this patent is extended or adjusted under 35 U.S.C. 154(b) by 0 days.

(21) Appl. No.: 11/221,279

(22) Filed: Sep. 7, 2005

(65) Prior Publication Data

US 2006/0052642 A1    Mar. 9, 2006

Related U.S. Application Data

(60) Provisional application No. 60/608,390, filed on Sep. 9, 2004.

(51) Int. Cl.
*C07C 209/66* (2006.01)
(52) U.S. Cl. ..................................................... 564/414
(58) Field of Classification Search .................... None
See application file for complete search history.

(56) References Cited

OTHER PUBLICATIONS

Barney, CL et al., Tetrahedron Letters, p. 5547-5550 (1990), "A convenient synthesis of hindered amines and alpha-trifluoromethylamines from ketones".
Demir, AS et al., Tetrahedron: Asymmetry, p. 2309-2313 (2001), "An asymmetric synthesis of both enantiomers of 2,2,2-trifluoro-1-furan-2-yl-ethylamine and 3,3,3-trifluoroalanine from 2,2,2-trifluoro-1-furan-2-yl-ethanone".
Enders, D et al., Organic Letters, p. 1575-1577 (2001), "Efficient asymmetric synthesis of alpha-trifluoromethyl-substituted primary amines via nucleophilic 1,2-addition to trifluoroacetaldehyde SAMP- or RAMP-hydrazone".
Gosselin, F et al., Organic Letters, p. 641-644 (2004), "Oxazolidine ring opening and isomerization to (E)-imines. Asymmetric synthesis of aryl-alpha-fluoroalkyl amino alcohols".

Ishii, A et al., Chemistry Letters, p. 119-120 (1998), "Stereospecific reduction with retention of chiral fluoral-derived 1,3-oxazolidines with LiAlH4: Asymmetric synthesis of 1-substituted 2,2,2-trifluoroethylamines".
Ishii, A et al., Synlett, p. 1381-1382 (1997), "Asymmetric addition reactions of grignard reagents to chiral fluoral hemiacetal: asymmetric synthesis of 1-substituted-2,2,2-trifluoroethylamines".
Ishii, A et al., Tetrahedron Letters, p. 1199-1202 (1998), "Stereocontrol at the quaternary center is 1-substituted 1-phenyl-2,2,2-trifluoroethylamines: stereospecific substitution with retention of a chiral cyclic fluoral N,O-acetal with organolithium reagents".
Pirkle, WH et al., J. Org. Chem., p. 2436-2439 (1977), "Design of chiral derivatizing agents for the chromatographic resolution of optical isomers. Asymmetric synthesis of some chiral fluoroalkylated amines".
Prakash, GK et al., Organic Letters, p. 2847-2850 (2001), "Asymmetric synthesis of trifluoromethylated allylic amines using alpha,beta-unsaturated N-tert-butanesulfinimines".
Prakash, GK et al., Angew. Chem. Int. Ed., p. 589-590 (2001), "Stereoselective nucleophilic trifluoromethylation of N-(tert-butylsulfinyl)-imines by using trimethyl(trifluoromethyl)-silane".
Soloshonok, VA et al., J. Org. Chem., p. 3030-3031 (1997), "Highly enantioselective transfer of chirality from a less to a more configurationally unstable stereogenic center. A practical asymmetric synthesis of (fluoroalkyl)amines via biomimetic transamination".
Wang, Y et al., Tetrahedron Letters, p. 987-990 (1991), "19F NMR Non-equivalence of diastereomeric amides of 2,2,2-trifluoro-1-phenylethylamine".

*Primary Examiner*—Brian Davis
(74) *Attorney, Agent, or Firm*—Nicole M. Beeler; Mark R. Daniel

(57) ABSTRACT

This invention describes the reaction of an alpha fluoroalkyl ketone with a bis(trialkylsilyl)amide to give a stable N-trialkylsilyl imine. Treatment of the N-trialkylsilyl imine with an alcohol leads to solvolysis of the trialkylsilyl group and yields a stable mixture of an aminal and an imine in high yield. Catalytic reduction of this mixture, or of the individual components, in the presence of a chiral catalyst leads to a fluoroalkyl amine with high enantioselectivity and high yield.

8 Claims, No Drawings

SYNTHESIS OF ALPHA FLUOROALKYL AMINES

This application claims benefit from Ser. No. 60/608,390 filed Sep. 9, 2004.

BACKGROUND OF THE INVENTION

The direct asymmetric synthesis of chiral alpha fluoroalkyl amines poses a considerable synthetic challenge. Currently known procedures involve the use of a chiral auxiliary on the nitrogen atom. For imines derived from ketones, diastereoselective reduction protocols are used with low to moderate selectivity. In the case of imines derived from aldehydes, diastereoselective nucleophilic addition protocols are used. All of these procedures require additional steps to install and remove an expensive and not always commercially available chiral auxiliary. The present invention does not require the use of a chiral auxiliary and yields fluoroalkyl amines with high enantioselectivty and high yield.

SUMMARY OF THE INVENTION

By this invention, there are provided processes for the preparation of compounds of structural formulas IA and IB:

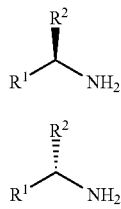

IA.

IB.

comprising the steps of:
a. Combining an alpha fluoroalkyl ketone of formula II in the presence of a bis(trialkylsilyl)amide to form an N-trialkylsilyl imine of formula III,

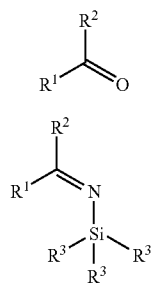

II.

III.

b. Reducing the N-trialkylsilyl imine of formula III to produce a compound of formula IA or IB;
wherein $R^1$ is aryl or heteroaryl;
$R^2$ is $C_{1-5}$ haloalkyl;
$R^3$ is $C_{1-6}$ alkyl.

DETAILED DESCRIPTION OF THE INVENTION

By this invention, there are provided processes for the preparation of compounds of structural formulas IA and IB:

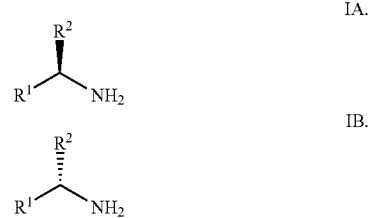

IA.

IB.

comprising the steps of:
a. Combining an alpha fluoroalkyl ketone of formula II in the presence of a bistrialkylsilylamide to form an N-trialkylsilyl imine of formula III,

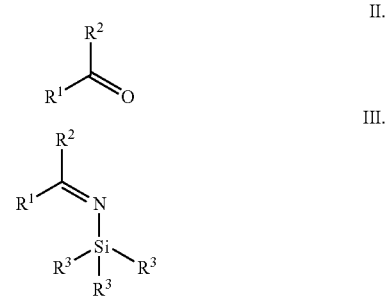

II.

III.

b. Reducing the N-trialkylsilyl imine of formula III to produce a compound of formula IA or IB;
wherein $R^1$ is aryl or heteroaryl;
$R^2$ is $C_{1-5}$ haloalkyl; and
$R^3$ is $C_{1-6}$ alkyl.

In an embodiment of the invention, the bis(trialkylsilyl)amide is lithium bis(trimethylsilyl)amide, sodium bis(trimethylsilyl)amide or potassium bis(trimethylsilyl)amide.

In an embodiment of the invention, an N-trialkylsilyl imine of formula III is treated with an alcohol of formula $R^4OH$ to yield a mixture of an aminal of formula IV and isomeric imines of formula V:

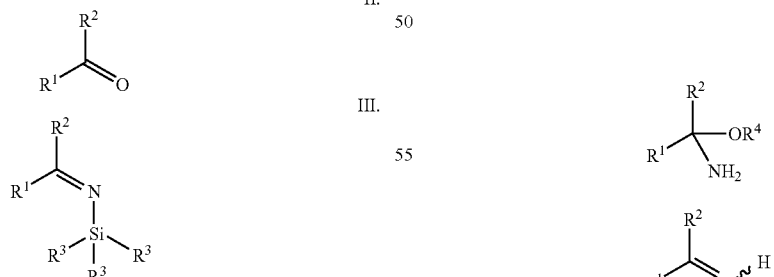

IV.

V.

wherein $R^4$ is $C_{1-5}$ alkyl. In a class of the invention, the alcohol is methanol, ethanol, n-propanol, 2-propanol, or a mixture thereof.

In an embodiment of the invention, the mixture of the aminal of formula IV and the isomeric imines of formula V, or the individual components, are reduced with a reducing agent in the presence of a chiral catalyst to yield the compound of formula I. In a class of the invention, the chiral catalyst is derived from an aminoalcohol and is of general structure:

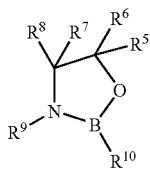

wherein $R^5$ is hydrogen or aryl;

$R^6$ is hydrogen or aryl;

$R^7$ is hydrogen or $C_{1-5}$ alkyl;

$R^8$ is hydrogen or $C_{1-5}$ alkyl;

$R^9$ is hydrogen or $C_{1-5}$ alkyl;

or $R^8$ and $R^9$ can be taken together with the carbon and nitrogen atom to which they are attached and form a 5 or 6 membered nitrogen containing ring; and $R^{10}$ is hydrogen or $C_{1-5}$ alkyl or aryl.

In a subclass of the invention, $R^5$ is phenyl. In a subclass of the invention, $R^6$ is phenyl. In a subclass of the invention, $R^7$ is hydrogen. In a subclass of the invention, $R^8$ and $R^9$ are taken together with the carbon and nitrogen atom to which they are attached and form a 5 membered nitrogen containing ring.

In a subclass of the invention, the amino alcohol is (R) or (S) diphenyl-2-pyrrolidine methanol.

In a class of the invention, the reducing agent is a boron hydride. In a subclass of the invention, the boron hydride is borane dimethylsulfide, borane tetrahydrofuran or catechol borane. Exemplifying the invention is catechol borane.

The term "alkyl" as used herein shall mean a substituting univalent group derived by conceptual removal of one hydrogen atom from a straight or branched-chain acyclic saturated hydrocarbon (i.e., —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, etc.).

As used herein, "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo. The term "keto" means carbonyl (C═O). The term "alkoxy" as used herein means an alkyl portion, where alkyl is as defined above, connected to the remainder of the molecule via an oxygen atom. Examples of alkoxy include methoxy, ethoxy and the like.

The term "haloalkyl" means an alkyl radical as defined above, unless otherwise specified, that is substituted with one to five, preferably one to three halogen. Representative examples include, but are not limited to trifluoromethyl, dichloroethyl, and the like.

In the schemes and examples below, various reagent symbols and abbreviations have the following meanings:

$BH_3Me_2S$: Borane methyl sulfide

HCl: Hydrochloric acid

LiHMDS: Lithium Hexamethyldisilazide $MgSO_4$: Magnesium sulfate

MTBE: Methyl tertiary butyl ether

NaOH: Sodium hydroxide

THF: Tetrahydrofuran

The compounds of the present invention can be prepared according to the following general scheme, using appropriate materials, and are further exemplified by the subsequent specific examples. The compounds illustrated in the examples are not, however, to be construed as forming the only genus that is considered as the invention. Those skilled in the art will readily understand that known variations of the conditions and processes of the following preparative procedures can be used to prepare these compounds. All temperatures are degrees Celsius unless otherwise noted.

SCHEME

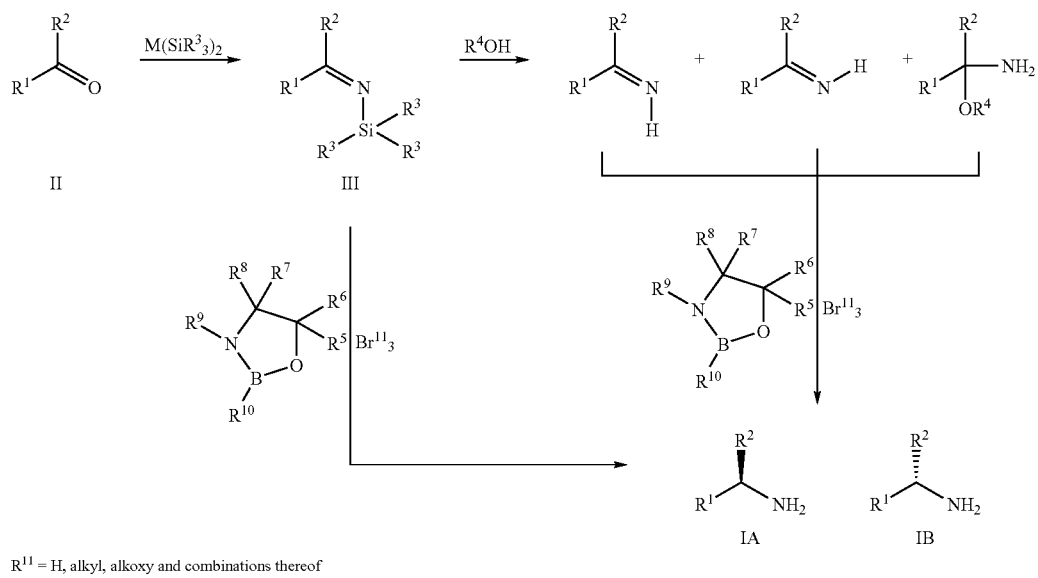

R[11] = H, alkyl, alkoxy and combinations thereof

EXAMPLE 1

(RS)-1-PHENYL-2,2,2-TRIFLUOROETHYLAMINE

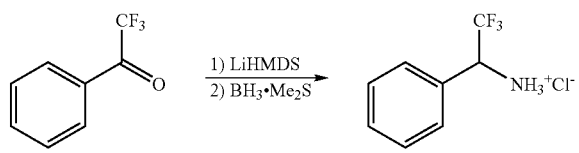

2,2,2-Trifluoromethyl acetophenone (491 mg, 2.82 mmol) was dissolved in toluene (10 mL) at rt. A solution of lithium bis(trimethylsilylamide) (3.15 mL, 3.15 mmol, 110 mol %, 1M in THF) was added over a 10 min period. The reaction was let stir at rt for 15 min and BH$_3$.Me$_2$S (2.82 mL, 5.73 mmol, 2M in toluene) was added. The reaction mixture was let stir at rt for 20 min. After cooling to 0° C., aqueous 2N NaOH (4 mL) was carefully added dropwise over 5 min. The mixture was stirred at rt for 90 min. The layers were separated and the organic layer was washed with aqueous 2N NaOH (5 mL) and water (5 mL), dried with MgSO$_4$ and filtered. To the solution of crude free amine in toluene was added a solution of hydrogen chloride (1 mL, 4M in 1,4-dioxane or 2 mL, 2M in diethyl ether). A white precipitate formed. After standing at rt for 1 h, the slurry was filtered and the solids were washed with MTBE (10 mL) to afford (RS)-1-phenyl-2,2,2-trifluoroethylamine hydrochloride as a white powder: $^1$H NMR (CD$_3$OD) δ 7.52–7.58 (m, 5H), 5.37 (q, J=7.5, 1H); $^3$C NMR (CD$_3$OD) δ 132.0, 130.6, 129.8, 129.5, 124.8 (q, J=1115), 56.7 (q, J=130); $^{19}$F NMR (CD$_3$OD) δ 3.96 (d, J=7.5).

Examples 2 and 3 can be prepared by utilizing procedures similar to those described in Example 1.

EXAMPLE 2

(RS)-2,2-DIFLUORO-1-(4-BROMOPHENYL)ETHYLAMINE HYDROCHLORIDE

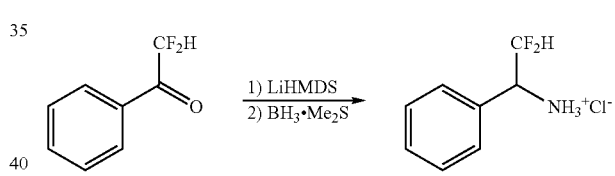

$^1$H NMR (CD$_3$OD) δ 7.69 (d, J=8.5 Hz, 2H), 7.44 (d, J=8.4 Hz, 2H), 6.33 (tq, J$_1$=54 Hz, J$_2$=2.8 Hz, 1H, —CF$_2$H), 4.84–4.8? (m, 1H, —CH(NH$_2$)(CF$_2$H)) $^{13}$C NMR (CD$_3$OD) δ 133.7, 131.4, 130.5, 125.6, 115.1 (t, J=975), 56.5–56.8 (m, 1H); $^{19}$F NMR (CD$_3$OD) δ −46.12 (d, J=306), −52.4 (d, J=306). HRMS calcd for C$_8$H$_9$F$_2$NBr [M+H]: 235.9886; found: 235.9883.

EXAMPLE 3

(RS)-2,2,3,3,3-PENTAFLUORO-1-PHENYLETHYLAMINE HYDROCHLORIDE

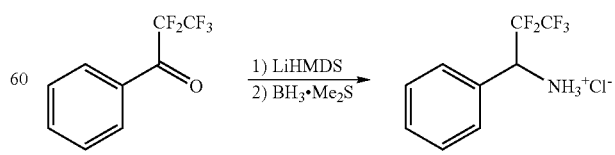

$^1$H NMR (CD$_3$OD) δ 7.53–7.59 (m, 5H), 5.47 (dd, J$_1$=22, J$_2$=6.7, 1H) $^{13}$C NMR (CD$_3$OD) δ 132.3, 130.7, 130.2, 129.3, 119.5 (qt, J$_1$=1137, J$_2$=136), 114.7 (tq, J$_1$=1039, $J_2=49$), 55.5 (t, J=83); $^{19}$F NMR (CD$_3$OD) δ−3.93, −38.7 (dd, $J_1$=287 Hz, $J_2$=2.7 Hz), −48.4 (dd, $J_1$=287 Hz, $J_2$=23 Hz). HRMS calcd for C$_9$H$_9$F$_5$N [M+H]: 226.0655; found: 226.0655.

EXAMPLE 4

1-(4-BROMOPHENYL)-2,2,2-TRIFLUOROETHYL-N-TRIMETHYLSILYLIMINE 1-(4-bromophenyl)-2,2,2-trifluoroethanone (6.0 g, 23.73 mmol) was dissolved in toluene (23 mL) and the solution was cooled to 0° C. A solution of lithium bis(trimethylsilylamide) (24 mL, 24 mmol, 110 mol %, 1M in THF) was added over 10 min. The solution was let stir at 0° C. for 1 h. Water (20 mL) was added and the layers were separated. The organic layer was washed with water (2×10 mL), dried with MgSO$_4$, filtered, and concentrated to afford crude N-TMS imine as a yellow oil: $^1$H NMR (CDCl$_3$) δ 7.55 (d, 2H, J=8.7), 7.48 (d, 2H, J=8.0), 0.20 (s, 9H); $^{13}$C NMR (CDCl$_3$) δ 156.2 (q, J=135) 134.0, 131.3, 129.2, 125.4, 117.4 (q, J=1144), 0.09; $^{19}$F NMR (CDCl$_3$) δ 8.57.

Examples 5–11 can be prepared by utilizing procedures similar to those described in Example 4.

EXAMPLE 5

N-(TRIMETHYLSILYL)-1-PHENYL-1-(2,2,2-TRIFLUOROMETHYL)KETIMINE

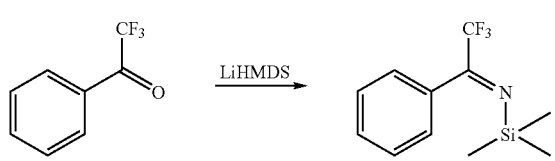

$^1$H NMR (CDCl$_3$) δ 7.54 (d, 2H, J=7.7), 7.44–7.48 (m, 1H), 7.39–7.43 (m, 2H), 0.16 (s, 9H); $^{13}$C NMR (CDCl$_3$) δ 158.8 (q, J=135), 135.7, 130.6, 127.7, 117.9 (q, J=1142), 0.25; $^{19}$F NMR (CDCl$_3$) δ 7.83.

EXAMPLE 6

N-(TRIMETHYLSILYL)-1-(3-BROMOPHENYL)-1-(2,2,2-TRIFLUOROMETHYL)KETIMINE

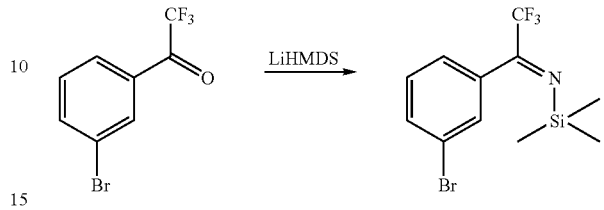

$^1$H NMR (CDCl$_3$) δ 7.72 (s, 1H), 7.60 (d, 1H, J=8.0), 7.51 (d, 1H, J=8.0), 7.26–7.31 (m, 1H), 0.20 (s, 9H); $^{13}$C NMR (CDCl$_3$) δ 156.2 (q, J=137), 137.3, 133.7, 130.8, 129.8, 126.3, 122.5, 117.5 (q, J=1143), 0.25; $^{19}$F NMR (CDCl$_3$) δ 8.39.

EXAMPLE 7

N-(TRIMETHYLSILYL)-1-(2-METHANESULFANYLPHENYL)-1-(2,2,2-TRIFLUOROMETHYL)KETIMINE

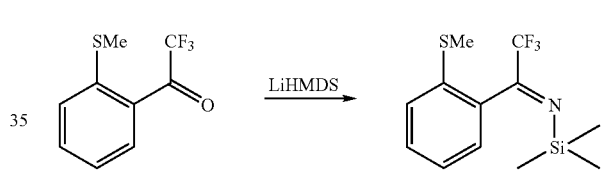

$^1$H NMR (CDCl$_3$) δ 7.37–7.41 (m, 1H), 7.30–7.31 (m, 1H), 7.17–7.20 (m, 1H), 7.10–7.12 (m, 1H), 2.48 (s, 3H), 0.03 (s, 9H); $^{13}$C NMR (CDCl$_3$) δ 160.9 (q, J=140), 136.9, 136.0, 130.0, 127.3, 126.7, 124.9, 117.9 (q, J=1417), 16.1, −0.70; $^{19}$F NMR (CDCl$_3$) δ 4.57.

EXAMPLE 8

N-(TRIMETHYLSILYL)-1-(3-METHANESULFANYLPHENYL)-1-(2,2,2-TRIFLUOROMETHYL)KETIMINE

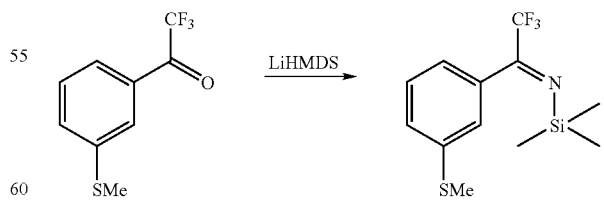

$^1$H NMR (CDCl$_3$) δ 7.40 (s, 1H), 7.33–7.34 (m, 1H), 7.31–7.32 (m, 1H), 7.28–7.31 (m, 1H), 2.50 (s, 3H), 0.17 (s, 9H); $^{13}$CNMR (CDCl$_3$) δ 158.0 (q, J=134), 139.2, 136.1, 128.6, 128.3, 125.3, 124.1, 118.0 (q, J=1142), 15.5, 0.2; $^{19}$F NMR (CDCl$_3$) δ 7.84.

EXAMPLE 9

N-(TRIMETHYLSILYL)-1-[2-PHENYL(PHENYL)]-1-(2,2,2-TRIFLUOROMETHYL) KETIMINE

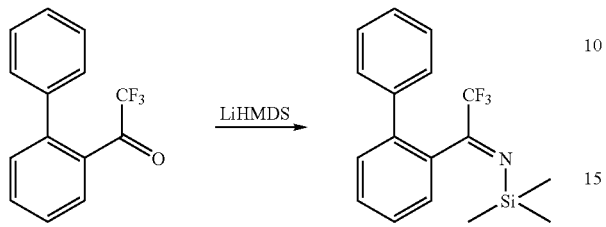

$^1$H NMR (CDCl$_3$) δ 7.48–7.51 (m, 1H), 7.42–7.44 (m, 1H), 7.37–7.41 (m, 3H), 7.29–7.36 (m, 4H), –016 (s, 9H); $^{13}$C NMR (CDCl$_3$) δ 162.1 (q, J=137), 140.4, 139.8, 135.8, 130.4, 129.8, 129.1, 128.5, 127.69, 127.67, 127.0, 117.7 (q, J=1137), –0.84; $^{19}$F NMR (CDCl$_3$) δ 6.52.

EXAMPLE 10

N-(TRIMETHYLSILYL)-1-(2-NAPHTHYL)-1-(2,2,2-TRIFLUOROMETHYL)KETIMINE

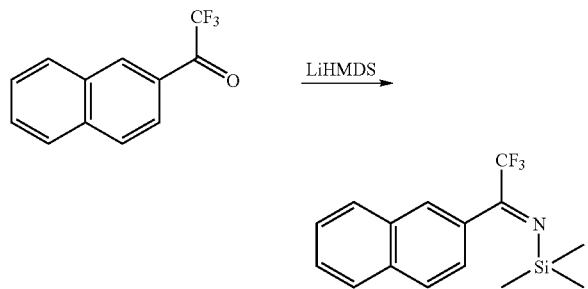

$^1$H NMR (CDCl$_3$) δ 8.07 (s, 1H), 7.90–7.94 (m, 1H), 7.86–7.87 (m, 2H), 7.69–7.70 (m, 1H), 7.53–7.58 (m, 2H), 0.21 (s, 9H); $^{13}$C NMR (CDCl$_3$) δ 158.1 (q, J=134), 134.2, 132.8, 132.5, 128.9, 128.2, 128.1, 127.7, 127.6, 126.7, 124.5, 118.0 (q, J=1154), 0.25; $^{19}$F NMR (CDCl$_3$) δ 8.88.

EXAMPLE 11

N-(TRIMETHYLSILYL)-1-(9-PHENANTHRYL)-1-(2,2,2-TRIFLUOROMETHYL)KETIMINE

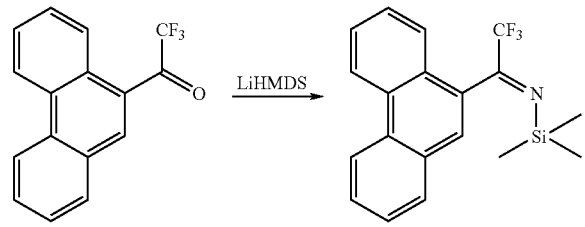

$^1$H NMR (CDCl$_3$) δ 8.74–8.75 (m, 1H), 8.71 (d, 1H, J=8.25), 7.91 (d, 1H, J=7.45), 7.70–7.75 (m, 3H), 7.64–7.67 (m, 2H), 7.62 (s, 1H), –0.12 (s, 9H); $^{13}$C NMR (CDCl$_3$) δ 162.5 (q, J=141), 133.3, 130.5, 130.20, 130.18, 129.3, 129.0, 127.8, 127.2, 127.15, 127.12, 126.2, 125.9, 123.1, 122.6, 118.4 (q, J=1133), –0.49; $^{19}$F NMR (CDCl$_3$) δ 4.14.

EXAMPLE 12

(S)-2,2,2-TRIFLUORO-1-(4-BROMOPHENYL) ETHYLAMINE HYDROCHLORIDE

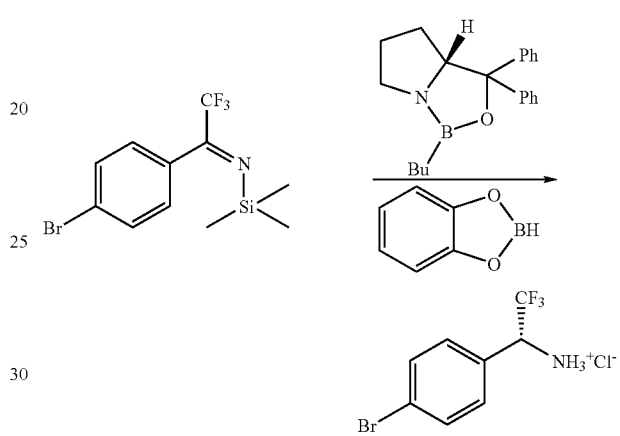

A solution of (R)-B-butyl-diphenylpyrrolidino-oxazoborolidine (0.3 mL, 0.094 mmol, 2.5 mol %, 0.3 M in toluene) was dissolved in toluene (1 mL), cooled to –15° C., and catecholborane (0.6 mL, 5.6 mmol, 150 mol %) was added to the solution. A solution of 1-(4-Bromophenyl)-2,2,2-trifluoroethyl-N-trimethylsilyl imine (1.2 g, 3.7 mmol) in toluene (4 mL) was added dropwise via syringe pump over a period of 2.5 h. After the addition was complete, the reaction mixture was let stir at –15° C. for 18 h. The reaction was quenched with aqueous 1N HCl (5 mL), let warm to rt and the layers were separated. The aqueous layer was basified with 10N NaOH to pH 12. The aqueous layer was extracted with MTBE (1×5 mL). The layers were separated and the organic layer was washed with aqueous 2N NaOH (2×5 mL), and water (5 mL). The organic layer was treated with Amberlite IRC-50S ion exchange resin (0.5 g) for 40 min to remove (S)-diphenylprolinol and filtered. The organic layer was dried and filtered. A solution of hydrogen chloride (4 mL, 2M in diethyl ether) was added to the crude solution of amine. A white precipitate formed. After aging at rt for 1 h, the slurry was filtered and the solids were washed with MTBE (1 mL) to afford (S)-2,2,2-trifluoro-1-(4-bromophenyl)ethylamine hydrochloride as a white powder (33% ee HPLC): $^1$H NMR (CD$_3$OD) δ 7.73 (d, 2H, J=8.5), 7.51 (d, 2H, J=8.5), 5.42 (q, 1H, J=7.4); $^{13}$C NMR (CD$_3$OD) δ 133.8, 131.6, 128.7, 126.3, 124.6 (q, J=1116), 55.9 (q, J=129); $^{19}$F NMR $^{19}$F NMR (CD$_3$OD) δ 3.90 (d, J=7.7). HRMS calcd for C$_8$H$_8$NF$_3$Br [M+H]: 253.9792; found: 253.9790.

EXAMPLE 13

1-(2,2,2-TRIFLUORO)-1-(4-BROMOPHENYL)ETHYLIMINE

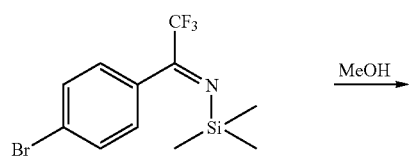

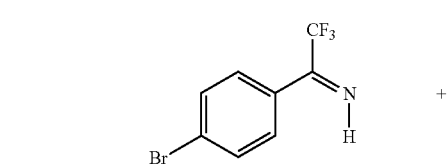

1-(4-bromophenyl)-2,2,2-trifluoroethyl-N-trimethylsilyl ketimine (4.517 g, 13.93 mmol) was dissolved in MeOH (10.7 mL) and stirred at rt for 18 h. The volatiles were removed under vacuum and the residue was flushed with toluene (3×20 mL) to afford crude NH-imine as a yellow-orange oil (3.33 g, 95% yield): A [65:19:16] mixture of (Z)/(E) imine isomers along with a methanol adduct: $^1$H NMR (CDCl$_3$) δ 10.82 (s, 1H, NH min.), 10.75 (s, 1H, NH maj.), 3,20 (s, 3H, —OMe); $^{13}$C NMR (CDCl$_3$) minor imine isomer: δ 165.4 (q, J=134), 120.0 (q, J=1112); major isomer: δ 162.0 (q, J=126), 118.1 (q, J=1121); MeOH adduct: δ 87.9 (q, J=118 Hz), 48.0; $^{19}$F NMR δ (CDCl$_3$) 8.47 (minor isomer); 7.48 (major isomer), −5.58 (methanol adduct).

Examples 14–18 can be prepared by utilizing procedures similar to those described in Example 13.

EXAMPLE 14

1-(2,2,2-TRIFLUORO)-1-(3-BROMOPHENYL)ETHYLIMINE+METHANOL ADDUCT

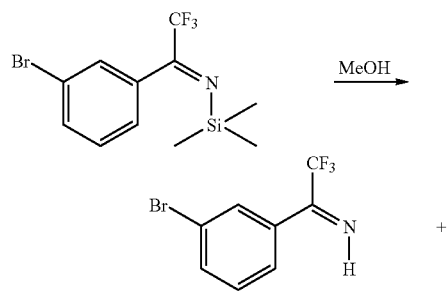

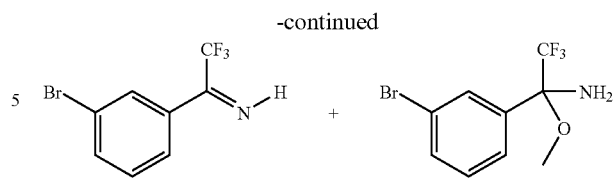

Isolated as a [41:15:44] mixture of (Z)/(E) N—H imine geometric isomers along with a methanol adduct as determined by $^1$H NMR spectroscopy in CDCl$_3$. Representative signals: $^1$H NMR (CDCl$_3$) δ 10.84 (s, minor), 10.82 (s, major), 3.21 (s, methanol adduct); $^{19}$F NMR (CDCl$_3$) δ 8.35 (minor), 7.42 (major), δ−5.47 (methanol adduct).

EXAMPLE 15

1-(2,2,2-TRIFLUORO)-1-(2-METHANESULFANYLPHENYL)ETHYLIMNE+METHANOL ADDUCT

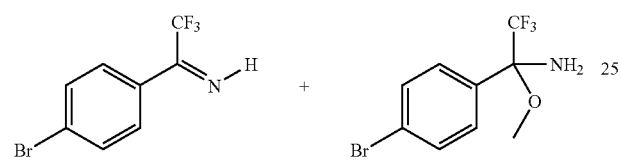

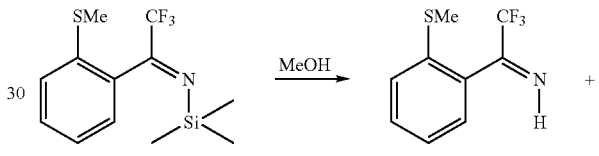

Isolated as a [1.8:1] mixture of (E)/(Z) N—H imine geometric isomers as determined by $^1$H NMR spectroscopy in CDCl$_3$. Representative signals: $^1$H NMR (CDCl$_3$) δ 11.3 (s, minor), 10.8 (s, major), 2.48; $^{13}$C NMR (CDCl$_3$) δ 166.6 (q, J=138, major), 163.6 (q, J=129, minor), 119.7 (q, J=1114 major), 117.7 (q, J=1124, minor); $^{19}$F NMR (CDCl$_3$) δ 6.57 (major), 5.68 (minor).

EXAMPLE 16

1-(2,2,2-TRIFLUORO)-1-(3-METHANESULFANYLPHENYL)ETHYLIMINE+METHANOL ADDUCT

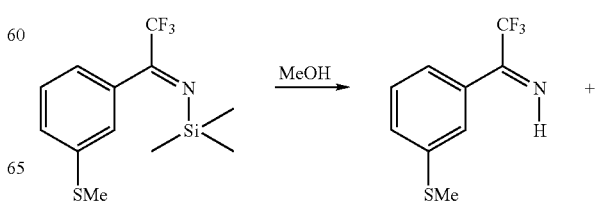

-continued

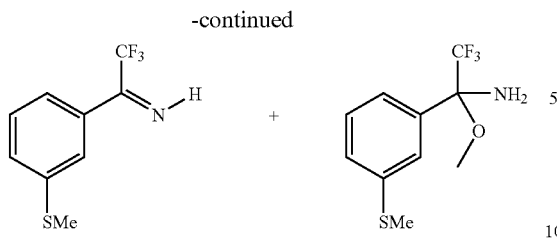

Isolated as a [57:23:20] mixture of (Z)/(E) N—H imine geometric isomers along with a methanol adduct as determined by $^1$H NMR spectroscopy in CDCl$_3$. Representative signals: $^1$H NMR (CDCl$_3$) δ 10.8 (s, minor), 10.7 (s, major), 3,21 (s, methanol adduct); $^{19}$F NMR (CDCl$_3$) δ 8.47 (minor), 7.66 (major), −5.59 (methanol adduct).

EXAMPLE 17

1-(2,2,2-TRIFLUORO)-1-(2-NAPHTHYL)ETH-YLIMINE+METHANOL ADDUCT:

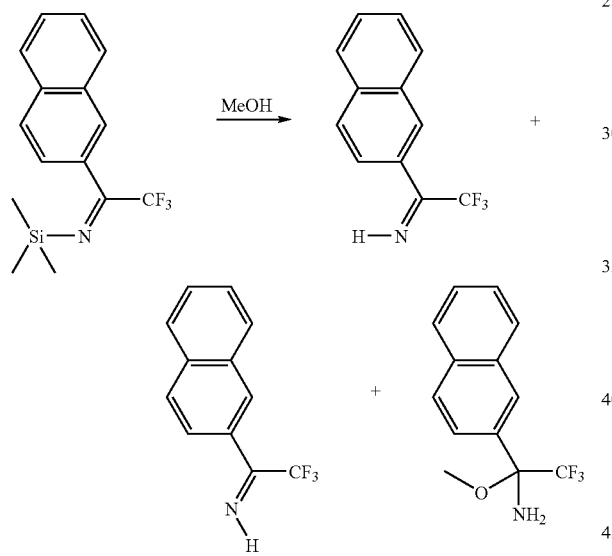

Isolated as a [45:15:46] mixture of (Z)/(E) N—H imine isomer along with a methanol adduct as determined by $^1$H NMR spectroscopy in CDCl$_3$. Representative signals: $^1$H NMR (CDCl$_3$) δ 10.92 (s, minor) 10.78 (s, major), 3.25 (s, methanol adduct); $^{19}$F NMR (CDCl$_3$) δ 9.02 (minor), 8.13 (major), −5.34 (methanol adduct).

EXAMPLE 18

1-(2,2,2-TRIFLUORO)-1-PHENYLETHYLIMNE+METHANOL ADDUCT

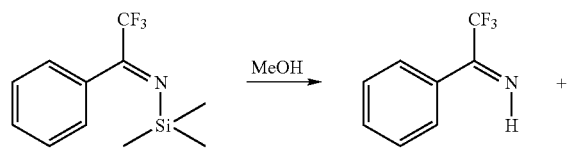

-continued

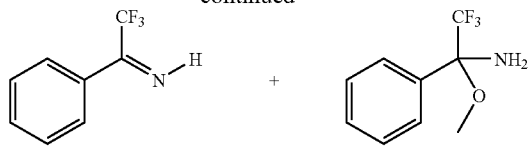

Isolated as a [18:8:74] mixture of (Z)/(E) N—H imine geometric isomers along with a methanol adduct as determined by $^1$H NMR spectroscopy in CDCl$_3$. Representative signals: $^1$H NMR (CDCl$_3$) δ 10.78 (s, minor), 10.69 (s, major), 3.21 (s, methanol adduct); $^{19}$F NMR (CDCl$_3$) δ 7.64 (major), 5.84 (minor), −5.72 (methanol adduct).

EXAMPLE 19

(S)-2,2,2-TRIFLUORO-1-(4-BROMOPHENYL)ETHYLAMINE HYDROCHLORIDE

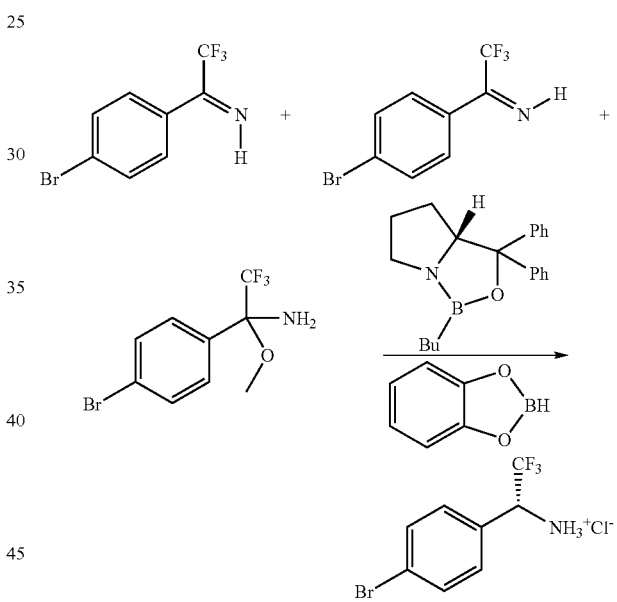

A solution of (R)-B-butyl-diphenylpyrrolidino-oxazoborolidine (3.14 mL, 0.94 mmol, 2.5 mol %, 0.3 M in toluene) was dissolved in toluene (10 mL), cooled to −15° C., and catecholborane (6.01 mL, 56.5 mmol, 150 mol %) was added to the solution. A solution of 1-(4-bromophenyl)-2,2,2-trifluoroethylimine (10.0 g, 37.6 mmol) in toluene (40 mL) was added dropwise via syringe pump over a period of 2.5 h. After the addition was complete, the reaction mixture was let stir at −15° C. for 18 h. The reaction was quenched with aqueous 1N HCl (50 mL), let warm to rt and the layers were separated. The aqueous layer was basified with 10N NaOH to pH 12. The aqueous layer was extracted with MTBE (1×50 mL). The layers were separated and the organic layer was washed with aqueous 2N NaOH (2×50 mL), and water (50 mL). The organic layer was treated with Amberlite IRC-50S ion exchange resin (5 g) for 40 min to remove (S)-diphenylprolinol and filtered. The organic layer was dried and filtered. A solution of hydrogen chloride (40 mL, 2M in diethyl ether) was added to the crude solution of amine. A white precipitate formed. After aging at rt for 1 h, the slurry was filtered and the solids were washed with MTBE (10 mL) to afford (S)-2,2,2-trifluoro-1-(4-bromophenyl)ethylamine hydrochloride as a white powder (91% ee HPLC): $^1$H NMR (CD$_3$OD) δ 7.73 (d, 2H, J=8.5), 7.51 (d, 2H, J=8.5), 5.42 (q, 1H, J=7.4); $^{13}$C NMR (CD$_3$OD) δ 133.8, 131.6, 128.7, 126.3, 124.6 (q, J=1116), 55.9 (q, J=129); $^{19}$F NMR $^{19}$F NMR (CD$_3$OD) δ 3.90 (d, J=7.7). HRMS calcd for C$_8$H$_8$NF$_3$Br [M+H]: 253.9792; found: 253.9790.

Examples 20–26 can be prepared by utilizing procedures similar to those described in Example 19.

EXAMPLE 20

(S)-2,2,2-TRIFLUORO-1-PHENYLETHYLAMINE HYDROCHLORIDE

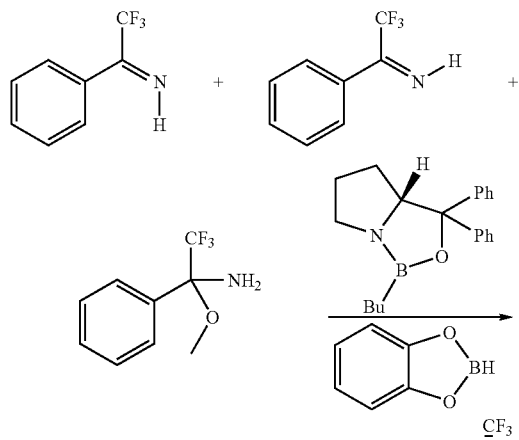

$^1$H NMR (CD$_3$OD) δ 7.52–7.58 (m, 5H), 5.37 (q, J=7.5 Hz, 1H, —CH(NH$_2$)(CF$_3$)). $^{13}$C NMR (CD$^3$OD) δ 132.0 (s), 130.6 (s), 129.8 (s), 129.5 (s), 124.8 (q, J=1115 Hz, —CF$_3$), 56.7 (q, J=130 Hz). $^{13}$F NMR (CD$_3$OD+CF$_3$Ph) δ 3.96 (d, J=7.5). HPLC 86% ee. HRMS calcd for C$_8$H$_9$F$_3$N [M+H]: 176.0687; found: 176.0689.

EXAMPLE 21

(S)-2,2,2-TRIFLUORO-1-(3-BROMOPHENYL) ETHYLAMINE HYDROCHLORIDE

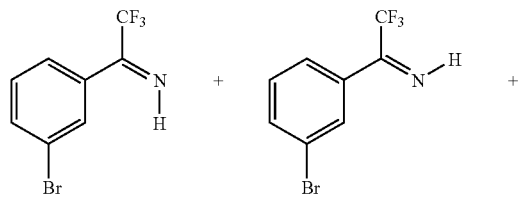

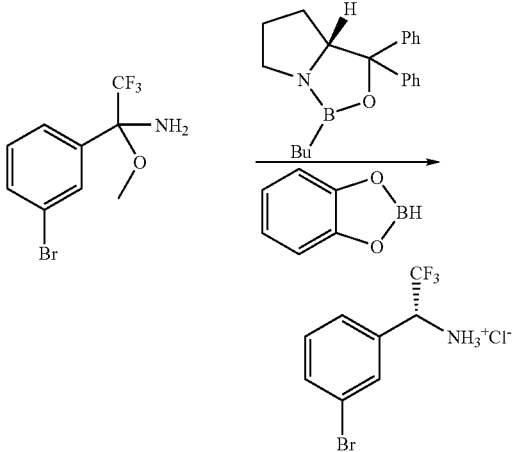

$^1$H NMR (CD$_3$OD) δ 7.80 (s, 1H), 7.75 (d, 1H, J=8.0), 7.58 (d, 1H, J=8.0), 7.48 (t, 1H, J=8.0), 5.44 (q, 1H, J=7.0); $^3$C NMR (CD$_3$OD) δ 135.2, 132.7, 132.4, 131.8, 128.6, 124.6 (q, J=1115), 124.2, 56.0 (q, J=131); $^{19}$F NMR (CD$_3$OD) δ 4.06 (d, J=7.8); HPLC 91% ee; HRMS calcd for C$_8$H$_9$F$_3$NBr [M=H]: 253.9792; found: 253.9794.

EXAMPLE 22

(S)-2,2,2-TRIFLUORO-1-[(2-METHANESULFANYL)PHENYL]ETHYLAMINE HYDROCHLORIDE

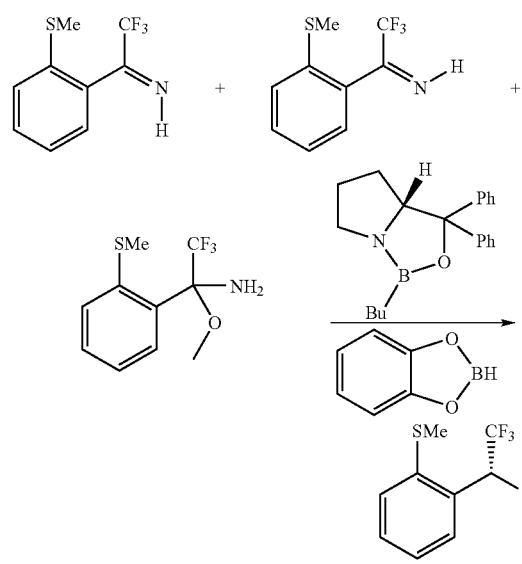

$^1$H NMR (CD$_3$OD) δ 7.63–7.67 (m, 2H), 7.54–7.57 (m, 1H), 7.41–7.45 (m, 1H), 5.86 (q, 1H, J=7.3), 2.55 (s, 3H); $^{13}$C NMR (CD$_3$OD) δ 141.2, 132.7, 131.8, 128.9, 128.7, 128.3, 124.8 (q, J=1117), 53.1 (q, J=131), 18.3; $^{19}$F NMR (CD$_3$OD) δ 4.48 (d, J=7.6). HPLC 99% ee. HRMS calcd for C$_9$H$_{11}$F$_3$NS [M+H]: 222.0564; found: 222.0564.

EXAMPLE 23

(S)-2,2,2-TRIFLUORO-1-[(3-METHANESULFA-NYL)PHENYL]ETHYLAMINE HYDROCHLORIDE

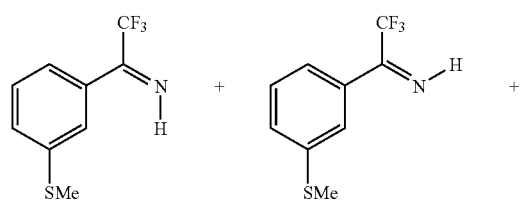

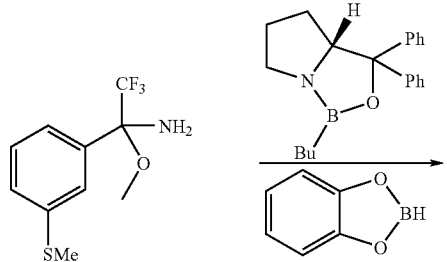

$^1$H NMR (CD$_3$OD) δ 7.43–7.47 (m, 3H), 7.32 (d, 1H, J=6.85), 5.37 (q, 1H, J=7.45), 2.52 (s, 3H); $^{13}$C NMR (CD$_3$OD) δ 142.5, 130.9, 130.3, 129.4, 126.9, 125.8, 124.7 (q, J=1115), 56.5 (q, J=129 Hz); $^{19}$F NMR (CD$_3$OD) δ 4.08 (d, J=7.7 Hz); HPLC 85% ee. HRMS calcd for C$_9$H$_{11}$F$_3$NS [M+H]: 222.0564; found: 222.0562.

EXAMPLE 24

(S)-2,2,2-TRIFLUORO-1-[(2-PHENYL)PHENYL]ETHYLAMINE HYDROCHLORIDE

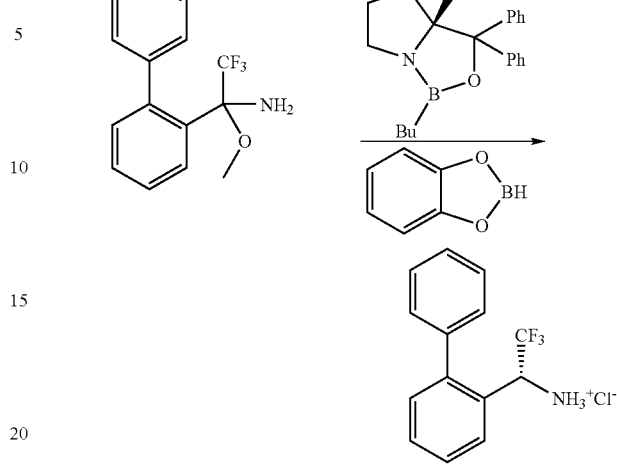

$^1$H NMR (CD$_3$OD) δ 7.79–7.82 (m, 1H), 7.60–7.64 (m, 2H), 7.45–7.54 (m, 2H), 7.41–7.43 (m, 1H), 7.33–7.35 (m, 2H), 5.07 (q, 1H, J=7.25); $^{13}$C NMR (CD$_3$OD) δ 145.4, 140.3, 132.3, 131.8, 130.3, 130.0, 129.9, 129.3, 128.4, 126.9, 124.7 (q, J=1118 Hz), 53.2 (q, J=130); $^{19}$F NMR (CD$_3$OD) δ 4.86 (d, J=7.6 Hz). HPLC 99% ee. HRMS calcd for C$_{14}$H$_{12}$F$_3$N [M+H]: 252.1000; found: 252.0998.

EXAMPLE 25

(S)-2,2,2-TRIFLUORO-1-(2-NAPHTHYL)ETHYLAMINE HYDROCHLORIDE

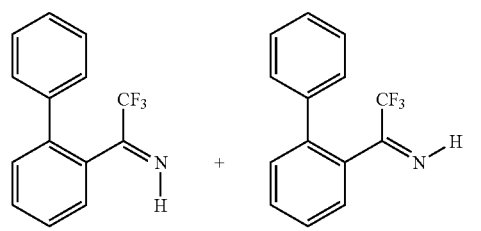

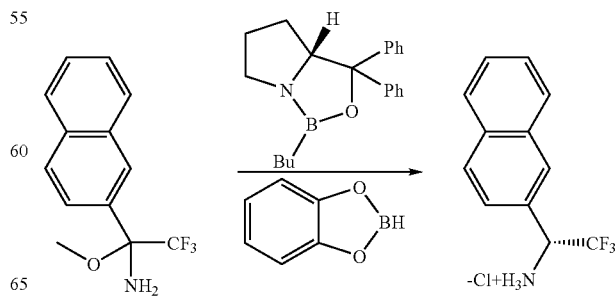

¹H NMR (CD₃OD) δ 8.12 (s, 1H), 8.05 (d, 1H, J=8.6), 7.95–7.98 (m, 2H), 7.59–7.63 (m, 3H), 5.55 (q, 1H, J=7.5); ¹³C NMR (CD₃OD) δ 135.4, 134.3, 130.6, 130.4, 129.4, 129.0 128.9, 128.4, 126.7, 125.4, 125.0 (q, J=1116), 56.9 (q, J=130); ¹⁹F NMR (CD₃OD) δ 4.25 (d, J=7.8 Hz); HPLC 75% ee. HRMS calcd for $C_{12}H_{11}F_3N$ [M+H]: 226.0844; found: 226.0848.

EXAMPLE 26

(S)-2,2,2-TRIFLUORO-1-(9-PHENANTHRYL) ETHYLAMINE HYDROCHLORIDE

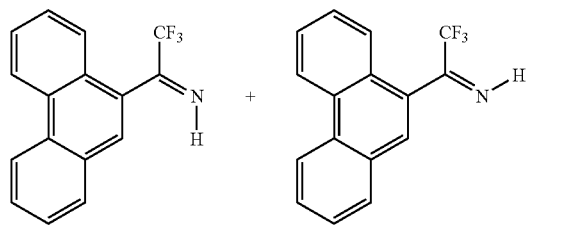

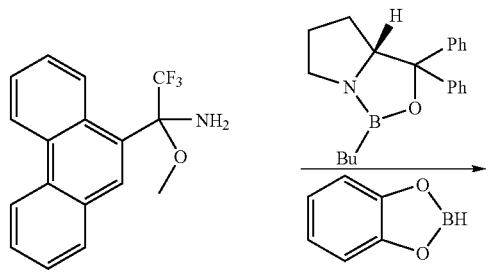

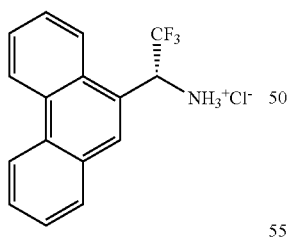

¹H NMR (CD₃OD) δ 8.94 (d, 1H, J=7.55), 8.85 (d, 1H, J=8.45), 8.29 (d, 1H, J=7.45), 8.15 (s, 1H), 8.03 (d, 1H, J=7.9), 7.77–7.83 (m, 3H), 7.71–7.74 (m, 1H), 6.36 (q, 1H, J=6.6); ¹³C NMR (CD₃OD) δ 132.3, 132.1, 131.5, 130.4, 130.3, 129.9, 129.2, 128.8, 128.7, 128.6, 125.2 (q, J=1118), 124.8, 124.6, 124.4, 123.8, 51.9 (q, J=130); ¹⁹F NMR (CD₃OD) δ 4.64. HPLC 99% ee. HRMS calcd for $C_{16}H_{13}F_3N$ [M+H]: 276.1000; found: 276.0999.

EXAMPLE 27

(S)-2,2,2-TRIFLUORO-1-(4-BROMOPHENYL) ETHYLAMINE HYDROCHLORIDE

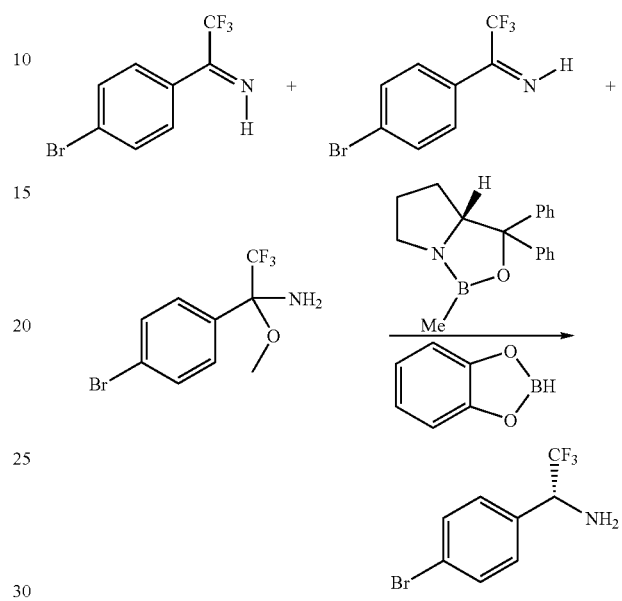

A solution of (R)-B-methyl-diphenylpyrrolidino-oxazoborolidine (1.88 mL, 1.88 mmol, 5 mol %, 1 M in toluene) was dissolved in toluene (12 mL), cooled to −15° C., and catecholborane (28.23 mL, 56.46 mmol, 150 mol %, 2 M in toluene) was added to the solution. A solution of 1-(4-bromophenyl)-2,2,2-trifluoroethylimine (10 g, 37.6 mmol) in toluene (40 mL) was added dropwise via syringe pump over a period of 2.5 h. The same workup as in the previous example afforded (S)-2,2,2-trifluoro-1-(4-bromophenyl)ethylamine hydrochloride as a white powder (91% ee HPLC).

What is claimed is:

1. A process for preparing a compound of formula IA or IB:

comprising the steps of:

a. Combining an alpha fluoroalkyl ketone of formula II in the presence of a bistrialkylsilylamide to form an N-trialkylsilyl imine of formula III,

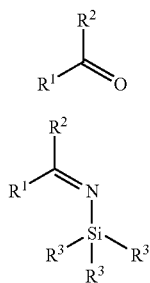

b. Reducing the N-trialkylsilyl imine of formula III to produce a compound of formula IA or IB;

wherein $R^1$ is aryl or heteroaryl;

$R^2$ is $C_{1-5}$ haloalkyl; and $R^3$ is $C_{1-6}$ alkyl.

2. The process of claim 1 wherein the bistrialkylsilylamide is lithium bistrimethylsilylamide, sodium bistrimethylsilylamide or potassium bistrimethylsilylamide.

3. The process of claim 2 wherein an N-trialkylsilyl imine of formula III is treated with an alcohol of formula $R^4OH$ to yield a mixture of an aminal of formula IV and an imine of formula V,

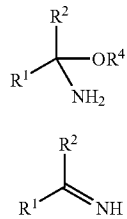

wherein $R^4$ is $C_{1-5}$ alkyl.

4. The process of claim 3 wherein the alcohol is methanol, ethanol, n-propanol, 2-propanol or a mixture thereof.

5. The process of claim 3 wherein the aminal of formula IV and the imine of formula V are reduced with a reducing agent in the presence of a chiral catalyst to yield the compound of formula IA or IB.

6. The process of claim 5 wherein the chiral catalyst is of general structure

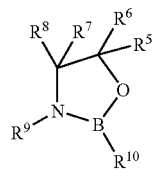

wherein $R^5$ is hydrogen or aryl;

$R^6$ is hydrogen or aryl;

$R^7$ is hydrogen or $C_{1-5}$ alkyl;

$R^8$ is hydrogen or $C_{1-5}$ alkyl;

$R^9$ is hydrogen or $C_{1-5}$ alkyl;

or $R^8$ and $R^9$ can be taken together with the carbon and nitrogen atom to which they are attached and form a 5 or 6 membered nitrogen containing ring; and $R^{10}$ is hydrogen or $C_{1-5}$ alkyl or aryl.

7. The process of claim 5 wherein the reducing agent is a boron hydride.

8. The process of claim 7 wherein the boron hydride is borane dimethylsulfide, borane tetrahydrofuran or catechol borane.

* * * * *